(12) United States Patent
Barker et al.

(10) Patent No.: US 10,517,553 B2
(45) Date of Patent: Dec. 31, 2019

(54) C-ARM IMAGING SYSTEM WITH MULTIPLE AUTOMATED INDEPENDENT ROTATIONAL AXES

(71) Applicant: General Electric Company, Schenectady, NY (US)

(72) Inventors: David Ellis Barker, Salt Lake City, UT (US); John Matthew Simmons, Salt Lake City, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 131 days.

(21) Appl. No.: 15/472,589

(22) Filed: Mar. 29, 2017

(65) Prior Publication Data

US 2018/0279980 A1    Oct. 4, 2018

(51) Int. Cl.
*A61B 6/00*    (2006.01)

(52) U.S. Cl.
CPC .......... *A61B 6/4441* (2013.01); *A61B 6/4405* (2013.01); *A61B 6/4429* (2013.01); *A61B 6/4435* (2013.01); *A61B 6/4447* (2013.01)

(58) Field of Classification Search
CPC ....... A61B 6/4435; A61B 6/4441; A61B 6/44; A61B 6/4429; A61B 6/4447
USPC ................................................. 378/196–198
See application file for complete search history.

(56) References Cited

U.S. PATENT DOCUMENTS

| | | | | |
|---|---|---|---|---|
| 4,298,801 A | * | 11/1981 | Heitman | A61B 6/4441 378/177 |
| 4,768,216 A | * | 8/1988 | Harvey | H05G 1/265 363/17 |
| 4,797,907 A | * | 1/1989 | Anderton | H05G 1/10 378/101 |
| 4,918,716 A | * | 4/1990 | Hahn | A61B 6/022 378/193 |
| 4,955,046 A | * | 9/1990 | Siczek | A61B 6/4405 378/197 |
| 4,987,585 A | * | 1/1991 | Kidd | A61B 6/4441 378/193 |
| 5,038,371 A | * | 8/1991 | Janssen | A61B 6/4441 378/193 |
| 5,386,453 A | * | 1/1995 | Harrawood | A61B 6/0442 378/193 |
| 5,583,909 A | * | 12/1996 | Hanover | A61B 6/4405 378/193 |
| 6,142,667 A | * | 11/2000 | Pattee | A61B 6/4405 378/197 |
| 6,428,206 B1 | * | 8/2002 | Watanabe | A61B 6/4233 378/197 |

(Continued)

FOREIGN PATENT DOCUMENTS

DE    100634421 A    7/2002

OTHER PUBLICATIONS

Arcadis Orbic/Orbic 3D: Enhanced Precision in the OR, 2010, Siemens AG, 20 pages.

*Primary Examiner* — Allen C. Ho
(74) *Attorney, Agent, or Firm* — Fletcher Yoder, P.C.

(57) ABSTRACT

An X-ray imaging system is provided. The X-ray imaging system includes an X-ray radiation source, an X-ray detector, and a C-arm. The C-arm has the X-ray radiation source disposed on a first end and the X-ray detector disposed on a second end opposite the first end. The X-ray imaging system also includes a motorized system configured to rotate the C-arm about three different rotational axes.

13 Claims, 3 Drawing Sheets

(56) References Cited

U.S. PATENT DOCUMENTS

| | | | |
|---|---|---|---|
| 6,461,039 B1* | 10/2002 | Klotz | A61B 6/4441 378/196 |
| 6,491,429 B1 | 12/2002 | Suhm | |
| 6,542,573 B2* | 4/2003 | Schomberg | G06T 11/005 378/19 |
| 6,582,120 B2* | 6/2003 | Schomberg | A61B 6/032 378/15 |
| 6,666,579 B2 | 12/2003 | Jensen | |
| 6,789,941 B1* | 9/2004 | Grady | A61B 6/4233 378/196 |
| 6,813,334 B2* | 11/2004 | Koppe | A61B 6/025 378/21 |
| 6,814,489 B2* | 11/2004 | Jensen | A61B 6/08 378/197 |
| 7,052,421 B2* | 5/2006 | Simmons | A61B 6/4405 378/197 |
| 7,218,702 B2* | 5/2007 | Mistretta | A61B 6/025 378/21 |
| 7,261,464 B2* | 8/2007 | Noda | A61B 6/4441 378/195 |
| 7,300,204 B2* | 11/2007 | Gotoh | A61B 6/4441 378/197 |
| 7,342,992 B2* | 3/2008 | Schomberg | A61B 6/032 378/19 |
| 7,478,949 B2* | 1/2009 | Niessen | A61B 6/08 378/197 |
| 7,491,940 B2* | 2/2009 | Graumann | G01T 1/2985 250/363.05 |
| 7,502,174 B2* | 3/2009 | Jensen | A61B 6/04 348/370 |
| 7,522,701 B2* | 4/2009 | Jensen | A61B 6/481 378/162 |
| 7,534,036 B2* | 5/2009 | Delmas | A61B 6/4441 378/196 |
| 7,591,587 B2* | 9/2009 | Gotoh | A61B 6/4441 378/189 |
| 7,607,832 B2* | 10/2009 | Jensen | A61B 6/4405 378/197 |
| 8,000,445 B2* | 8/2011 | Mollus | A61B 6/4441 378/4 |
| 8,047,715 B2* | 11/2011 | Noordhoek | A61B 6/035 378/194 |
| 8,170,317 B2* | 5/2012 | Movassaghi | A61B 6/0457 378/196 |
| 8,249,213 B2* | 8/2012 | Noordhoek | A61B 6/583 378/11 |
| 8,260,025 B2* | 9/2012 | Walimbe | A61B 6/5247 378/4 |
| 8,379,795 B2* | 2/2013 | Mabini | A61B 6/461 378/98 |
| 8,408,788 B2* | 4/2013 | Ozawa | A61B 6/102 378/197 |
| 8,643,642 B2* | 2/2014 | Mistretta | A61B 6/4441 345/419 |
| 8,712,138 B2* | 4/2014 | Gleich | A61B 6/4241 382/132 |
| 8,764,291 B2* | 7/2014 | Ruijters | A61B 5/06 378/195 |
| 8,768,031 B2* | 7/2014 | Mistretta | A61B 6/4441 382/128 |
| 8,899,834 B2* | 12/2014 | Barker | A61B 6/4405 250/370 |
| 9,113,821 B2* | 8/2015 | Matsumoto | A61B 6/4441 |
| 9,265,470 B2* | 2/2016 | Simmons | A61B 6/447 |
| 9,649,077 B2* | 5/2017 | Bouvier | A61B 6/102 |
| 9,693,437 B2* | 6/2017 | Simmons | G01N 23/04 |
| 10,405,821 B2* | 9/2019 | Hansis | A61B 5/4566 |
| 2002/0168053 A1 | 11/2002 | Schomberg | |

* cited by examiner

C-ARM IMAGING SYSTEM WITH MULTIPLE AUTOMATED INDEPENDENT ROTATIONAL AXES

BACKGROUND

The subject matter disclosed herein relates to X-ray imaging systems having C-arms and, more particularly, to X-ray imaging systems where the C-arm includes automated motion along multiple independent rotational axes.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to one end of a movable arm. In such cases, the C-arm can often be raised and lowered, be moved from side to side, and/or be rotated about one or more axes of rotation. Accordingly, such C-arms can be moved and reoriented to allow X-ray images to be taken from several different positions and angles and different portions of a patient, without requiring the patient to be frequently repositioned. However, rotation or motion of the C-arm may be limited in certain directions (e.g., orbital direction) due to the structure of the imaging system or lack of independent rotational axes.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In a first embodiment, an X-ray imaging system is provided. The X-ray imaging system includes an X-ray radiation source, an X-ray detector, and a C-arm. The C-arm has the X-ray radiation source disposed on a first end and the X-ray detector disposed on a second end opposite the first end. The X-ray imaging system also includes a motorized system configured to rotate the C-arm about three different rotational axes.

In a second embodiment, an X-ray imaging system is provided. The X-ray imaging system includes an X-ray radiation source, an X-ray detector, and a C-arm. The C-arm has the X-ray radiation source disposed on a first end and the X-ray detector disposed on a second end opposite the first end. The X-ray imaging system also includes a base coupled to the C-arm. The X-ray imaging system further includes a motorized system configured to rotate the C-arm at least 180 degrees in an orbital direction relative to where the C-arm is coupled to the base.

In a third embodiment, an X-ray imaging system is provided. The X-ray imaging system includes an X-ray radiation source, an X-ray detector, and a C-arm. The C-arm has the X-ray radiation source disposed on a first end and the X-ray detector disposed on a second end opposite the first end. The X-ray imaging system also includes a base, a horizontal arm coupled to the base, and an L-arm having a first end and a second end, where the first end is coupled to the horizontal arm. The X-ray imaging system further includes a C-arm rotation device configured to enable the C-arm to rotate in an orbital direction relative to the C-arm rotation device, wherein the C-arm rotation device is coupled to the second end of the L-arm. The X-ray imaging system even further includes a motorized system configured to rotate the C-arm about three different rotational axes.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following embodiments describe an X-ray imaging system (e.g., mobile X-ray imaging system) having automated C-arm motion about multiple independent (e.g., separate or different) rotational axes (e.g., 3 or more). For example, the C-arm may rotate about 3 different axes: a lateral axis, an orbital axis, and a flip-flop axis (e.g., defined by rotation about where the C-arm is coupled to an L-arm). The motion about these 3 different axes may be automated (e.g., via a motorized system including multiple motors or servomotors). The automated motion about these 3 different axes may increase the orbital range or coverage with the C-arm in the orbital direction to at least 180 degrees without having to move the patient and/or table the patient is disposed on. Motorization of all of these axes (especially the flip-flop axis) provides numerous advantages. For example, motorized motion compared to manual motion may be controlled remotely to reduce radiation exposure. In addition, motorization of all these axes enables the capture of image data for three-dimensional (3D) image generation about at least 180 degrees in the orbital direction, while still allowing the X-ray imaging system to be utilized as a general purpose C-arm imaging system. Typically, increasing the orbital motion to 180 degrees about a single axis keeps the imaging system from being utilized in general procedures (e.g., procedures in orthopedics, gastroenterology, cardiology, etc.). However by automating all of these axes, a general purpose C-arm imaging system may also be utilized as an accurate 3D image capturing imaging system.

Figure 1:
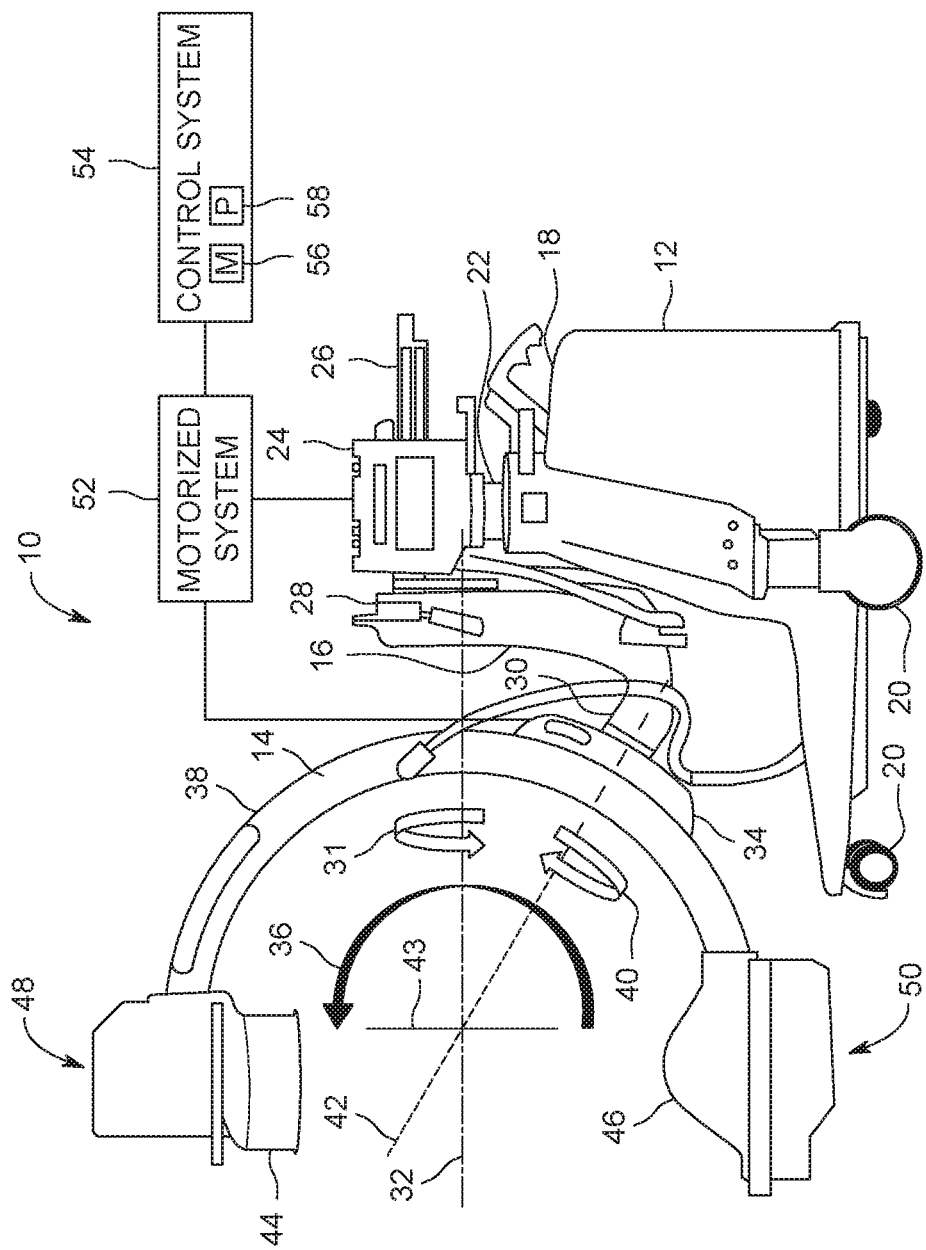
FIG. 1 is a side view of an embodiment of an X-ray imaging system (e.g., a mobile C-arm imaging system) having multiple independent rotational axes.

FIG. 1 is a side view of an embodiment of an X-ray imaging system 10 (e.g., a mobile C-arm imaging system) having multiple independent rotational axes. Although a mobile imaging system is illustrated, the embodiments described below may be utilized with any X-ray imaging system having a C-arm (e.g., a fixed imaging system). The X-ray imaging system 10 may utilize multiple imaging modalities (e.g., fluoroscopy, computed tomography, tomosynthesis, radiographic, magnetic resonance imaging, etc.) to acquire two-dimensional 2D and/or 3D image data. The X-ray imaging system 10 may be utilized for both diagnostic and interventional imaging. In addition, the X-ray imaging system 10 may be utilized for general purposes (e.g., general radiology, orthopedics, etc.) and special purposes (e.g., image guided surgery).

A principal function of the mobile X-ray imaging system 10 is to generate X-rays for diagnostic and interventional imaging. The X-ray imaging system 10 includes a support structure or base 12, a C-arm 14, an L-arm 16, and a control panel 18. The base 12 provides support for the C-arm 14 and holds the C-arm 14 in a suspended position. The lower portion of the base 12 includes wheels or casters 20 utilized to provide mobility to the X-ray imaging system 10. The base 12 includes a vertical lift column 22 that permits the C-arm 14 and L-arm 16 to move vertically in relation to base 12. Vertical lift column 22 terminates in an upper housing 24 of the base 12, wherein a horizontal extension arm 26 passes through upper housing 24 and permits L-arm 16 (as well as the C-arm 14) to move perpendicularly in relation to vertical lift column 22 by movement (e.g., horizontal movement) of the horizontal extension arm 26 in relation to upper housing 24. The C-arm 14 may be moved along the axis of the horizontal extension arm 26 to effect transverse tracking motion. The L-arm 16 is coupled to the horizontal extension arm 26 via end 28 and configured to pivot or rotate about the horizontal extension arm 26 such that the L-arm 16 can be made to pivot in a 360 degree arc. The horizontal extension arm 26 is coupled to one end 28 of the L-arm 16, while an outer end 30 of the L-arm 16 is coupled to C-arm 14. Rotation of the L-arm 16 about where it is coupled to the horizontal extension arm 26 enables the C-arm 14 to be rotated (e.g., 360 degrees) in a lateral direction 31 (e.g., circumferential direction) about a lateral axis 32 (e.g., parallel to the horizontal extension arm 26) relative to the base 12.

The C-arm 14 is coupled to a C-arm rotation device 34 (e.g., carriage) that is coupled to the end 30 of the L-arm 16. The C-arm rotation device 34 is coupled to an assembly of rollers or wheels (e.g., disposed within a track 38 of the C-arm 14) that enables the C-arm 14 to move or rotate about an orbital axis 36 in an orbital direction along the track 38 relative to C-arm rotation device 34. As described in greater detail below, the X-ray imaging system 10 is configured to enable the C-arm 14 to rotate at least 180 degrees in the orbital direction to provide an orbital range or coverage of at least 180 degrees relative to a location where the C-arm 14 is coupled to the base 12 (i.e., the C-arm rotation device 34).

The C-arm rotation device 34 also enables the C-arm 14 to rotate (e.g., circumferentially) or flip-flop (e.g., as indicated by reference numeral 40) about an axis 42 (e.g., flip-flop axis) emanating from where the C-arm rotation device 34 is coupled to the C-arm 14 and, thus, the base 12. The C-arm rotation device 34 enables 180 degrees of rotation of the C-arm relative to the C-arm rotation device 34.

Rotation of the L-arm 16 180 degrees (thereby enabling rotation about the lateral axis 32 and the flip-flop axis 42) enables the image chain to rotate 180 degrees about the orbital axis 36. An orbital plane 43 extends perpendicular to the orbital axis 36 and includes the image chain and the C-arm 14. The beginning and final orientation of the orbital plane 43 remains the same when the C-arm 14 is rotated 180 degrees about the lateral axis 32. However, during movement of the L-arm 16, the orbital plane 43 changes with the largest angular changer occurring when the L-arm 16 is rotated 90 degrees.

An image receptor 44 (e.g., X-ray detector) and an X-ray source 46 are coupled to opposing ends 48, 50 of the C-arm 14 to form an image chain. The C-arm 14 allows the image receptor 44 and the X-ray source 46 to be mounted and positioned about an object to be imaged, such as a patient. The C-arm 14 may be a circular C-shaped or an arc-shaped member, for example. The C-arm 14 enables selective positioning of the image receptor 44 and the X-ray source 46 with respect to the width and length of the patient or other object located within the interior free space of the C-arm 14. The image receptor 44 may be an image intensifier or other energy receptor for using in diagnostic imaging, for example. The image receptor 44 and the X-ray source 46 are used to generate a diagnostic image representative of the object being imaged.

Rotation about the axes 32, 36, and 42 are independent (e.g., separate or different from each other). Rotation of the C-arm 14 with respect to these axes 32, 36, 42 is driven by a motorized system 52. The motorized system 52 may include one or more motors or servomotors to drive the rotation about these axes 32, 36, 42 via automation. The motors or servomotors may be disposed throughout different components of the X-ray imaging system 10 (e.g., the upper housing 24 of base 12, the L-arm 16, the C-arm rotation device 34, the C-arm 14, etc.). The motorized system 52 may be coupled to control system or controller 54 (e.g., disposed within the base 12 and/or remote from the X-ray imaging system 10). The control system 54 may include a memory 56 and one or more processors 58 to execute code or instructions stored within the memory 56. The control system 52 may control the automated movement of the C-arm 14 about the axes 32, 36, 42.

The automated or motorized movement of the C-arm 14 about the independent axes 32, 36, 42 increases the orbital range or coverage about the orbital axis 36 (i.e., allows the C-arm 14 to be rotated 180 degrees in the orbital direction). In particular, the orbital range may be increased to 180 degrees or greater (e.g., up to at least approximately 205 degrees). In particular, orbital rotation of the C-arm 14 180 degrees is achieved by rotating the C-arm 14 180 degrees about the lateral axis 32 and 180 degrees about the flip-flop axis 42.

Figure 2:
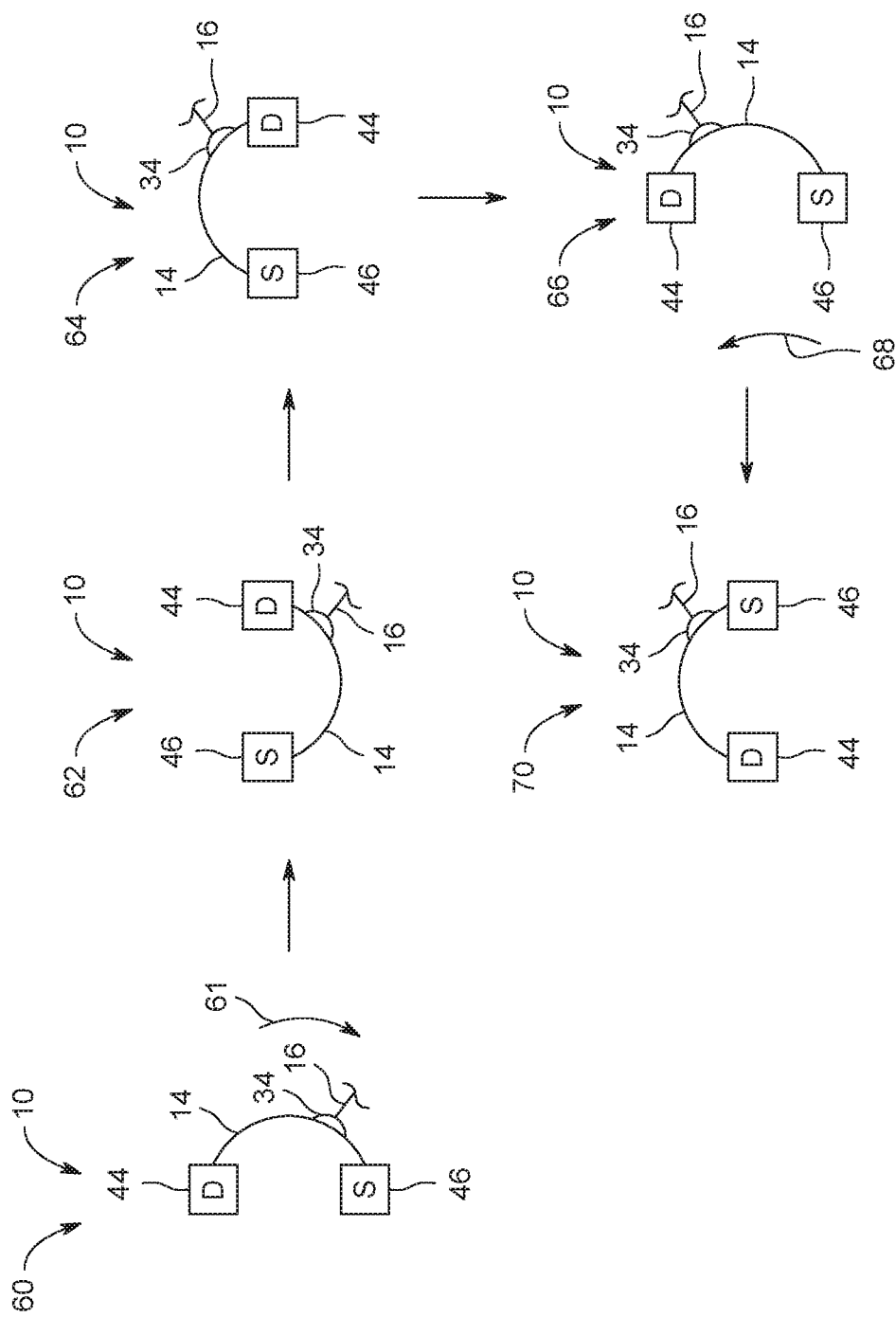
FIG. 2 is a schematic view of an embodiment of motion of a C-arm of the X-ray imaging system of FIG. 1 to achieve 180 degrees of orbital rotation.

FIG. 2 is a schematic view of an embodiment of motion of the C-arm 14 of the X-ray imaging system 10 of FIG. 1 to achieve 180 degrees of orbital rotation (e.g., for the acquisition of 3D image data). The sequence of the different positions or movements of the C-arm 14 may vary in order and/or be performed simultaneously in other embodiments to achieve 180 degrees of orbital motion. From a first position 60 (similar to shown in FIG. 1), the C-arm 14 is rotated in an orbital direction 61 into a second position 62 (e.g., under scan position). From the second position 62, the L-arm 16 is rotated (e.g., laterally) 180 degrees about the horizontal extension bar 26 to a third position 64. This results in both the lateral axis 32 and the flip-flop axis 42 (along with the C-arm 14) being rotated 180 degrees. From the third position 64, the orbital rotation device 34 (along with the C-arm 14) are rotated 180 degrees about the flip-flop axis 42 to a fourth position 66. From the fourth position 66, the C-arm 14 is rotated in an orbital direction 68 into a fifth position 70. A comparison of the second position 62 and the fifth position 70 illustrates 180 degrees of orbital rotation of the C-arm 14. This C-arm movement is possible due to the automated movement about the rotational axes 32, 36, 42 and is achieved without moving the patient and the table.

Figure 3:
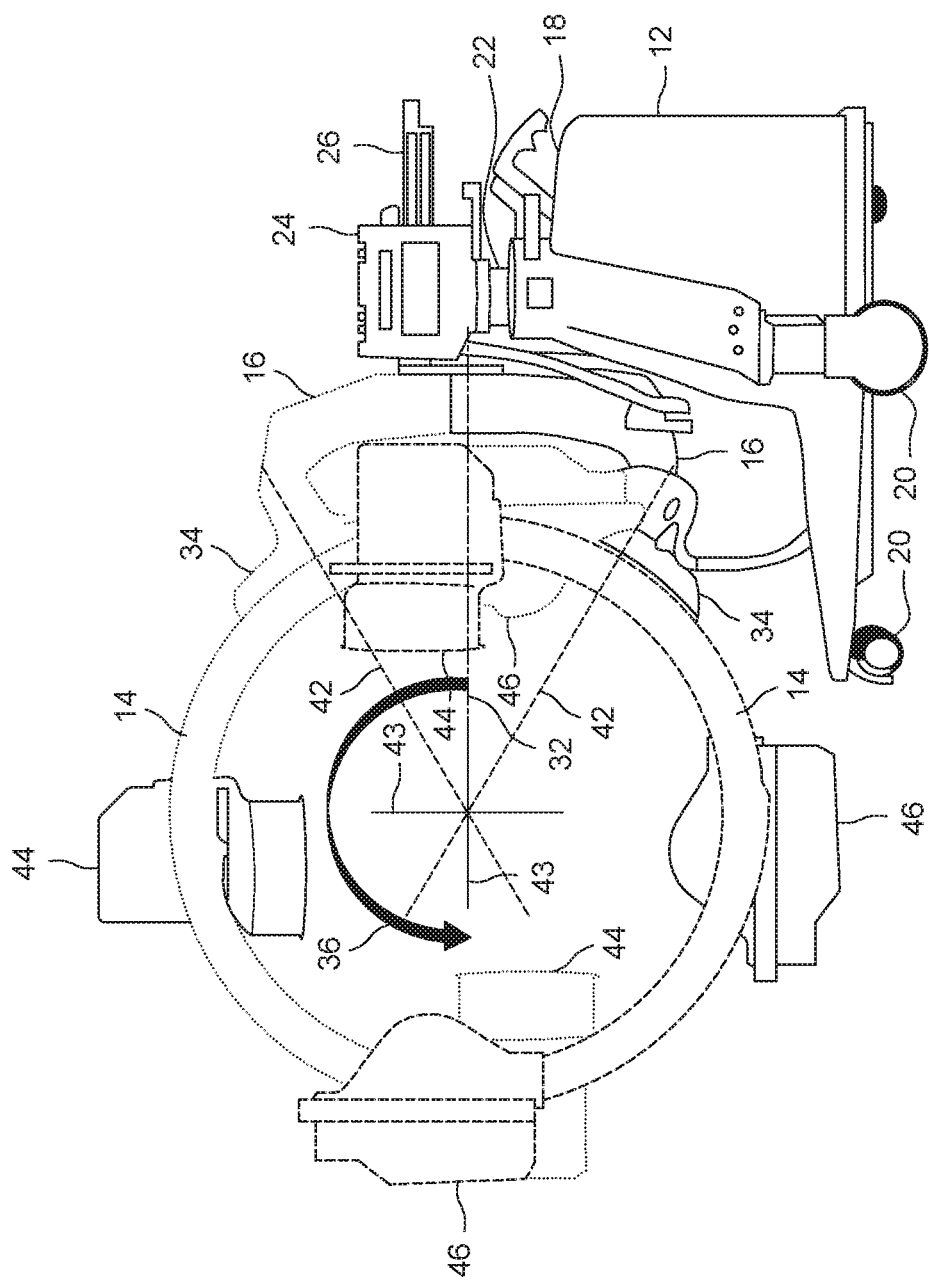
FIG. 3 is a side view of the X-ray imaging system of FIG. 1 with some of the positions in FIG. 2 superimposed.

FIG. 3 is a side view of the X-ray imaging system 10 of FIG. 1 with some of the positions in FIG. 2 superimposed. In particular, FIG. 3 depicts the C-arm 14 in the first position 60 (shown in solid lines) of FIG. 2. FIG. 3 also depicts the C-arm 14 in the second or under scan position 62 (shown in dashed lines) after rotating the C-arm 14 in the orbital direction 61 (see FIG. 2). FIG. 3 further depicts the C-arm 14 in the fifth position 70 (shown in dotted lines) after the combination of movements described above. A comparison of the second position 62 and the fifth position 70 illustrates 180 degrees of orbital rotation of the C-arm 14. Also, a comparison of the second position 62 and the fifth position 70 illustrates the orbital plane 43 is rotated 180 degrees. A comparison of the first position 60 to the fifth position 70 illustrates the orbital plane 43 has also shifted 90 degrees. As illustrated in FIG. 3, upon rotating the L-arm 16 180 degrees both the lateral axis 32 and the flip-flop axis 42 are also rotated 180 degrees.

The motorized movement about the axes 32, 36, 42 may occur at a same time and rate, where the movement about all of the axes 32, 36, 42 is from their initial position to 180 degrees. Alternatively, the motorized movement about the axes 32, 36, 42 at pre-defined non-linear rates. In certain embodiments, the motorized movement about the axes 32, 36, 42 may occur at different times (e.g., separately). In certain embodiments, the vertical lift column 22 may be utilized in the coordinated motion. In certain embodiments, multiple C-arms coupled to the C-arm 14 (e.g., in a nested arrangement) may be utilized (e.g., instead of the L-arm 16) similar to a rotation telescoping mechanism to enable the orbital plane 43 to be rotated 180 degrees.

Technical effects of the disclosed embodiments include providing an X-ray imaging system 10 (e.g., mobile X-ray imaging system) having automated C-arm motion about multiple independent (e.g., separate or different) rotational axes (e.g., 3 or more). For example, the C-arm 14 may rotate about 3 different axes: a lateral axis 32, orbital axis 36, and a flip-flop axis 42 (e.g., defined by rotation about where the C-arm 14 is coupled to an L-arm 16). The motion about these 3 different axes may be automated (e.g., via a motorized system 52 including multiple motors or servomotors). The automated motion about these 3 different axes may increase the orbital range or coverage with the C-arm 14 in the orbital direction to at least 180 degrees without having the move the patient and/or table the patient is disposed on. For example, motorization of all these axes enables the capture of 3D image data about at least 180 degrees in the orbital direction, while still allowing the X-ray imaging system 10 to be utilized as a general purpose C-arm imaging system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. An X-ray imaging system, comprising:
an X-ray radiation source;
an X-ray detector;
a C-arm having the X-ray radiation source disposed on a first end and the X-ray detector disposed on a second end opposite the first end;
a base coupled to the C-arm;
a motorized system configured to rotate the C-arm about three different rotational axes;
a C-arm rotation device; and
a horizontal arm coupled to the base and an L-arm having a first end coupled to the horizontal arm and a second end coupled to the C-arm via the C-arm rotation device, wherein the L-arm is configured to rotate about the horizontal arm to enable rotation of the C-arm in the lateral direction, and the C-arm rotation device is configured both to rotate about the second end of the L-arm to enable rotation of the C-arm about a location where the C-arm is coupled to the base and to rotate in the orbital direction;
wherein the motorized system is configured to rotate the C-arm at least 180 degrees in the orbital direction by rotating the C-arm about the three different rotational axes at both a same time and rate.

2. The X-ray imaging system of claim 1, wherein the motorized system is configured to rotate the C-arm at least 180 degrees in an orbital direction relative to a location where the C-arm is coupled to the base.

3. The X-ray imaging system of claim 2, wherein the motorized system is configured to rotate the C-arm at least 180 degrees in the orbital direction by both rotating the C-arm 180 degrees in a lateral direction relative to the base and rotating the C-arm 180 degrees about the location where the C-arm is coupled to the base.

4. The X-ray imaging system of claim 1, wherein the motorized system is configured to rotate the C-arm at least 180 degrees in the orbital direction by rotating the C-arm about the three different rotational axes at pre-defined non-linear rates.

5. The X-ray imaging system of claim 1, wherein the motorized system is configured to rotate the C-arm at least 180 degrees in the orbital direction by rotating the C-arm about the three different rotational axes at different times.

6. An X-ray imaging system, comprising:
an X-ray radiation source;
an X-ray detector;
a C-arm having the X-ray radiation source disposed on a first end and the X-ray detector disposed on a second end opposite the first end;
a base coupled to the C-arm; and
a motorized system configured to rotate the C-arm at least 180 degrees in an orbital direction relative to where the C-arm is coupled to the base, wherein the motorized system is configured to rotate the C-arm at least 180 degrees in the orbital direction by both rotating the C-arm 180 degrees in a lateral direction relative to the base and rotating the C-arm 180 degrees about a location where the C-arm is coupled to the base, and wherein the motorized system is configured to rotate the C-arm at least 180 degrees in the orbital direction by rotating the C-arm about three different rotational axes at both a same time and rate.

7. The X-ray imaging system of claim 6, comprising a C-arm rotation device, a horizontal arm coupled to the base, and an L-arm having a first end coupled to the horizontal arm and a second end coupled to the C-arm via the C-arm rotation device, wherein the L-arm is configured to rotate about the horizontal arm to enable rotation of the C-arm in the lateral direction, and the C-arm rotation device is configured both to rotate about the second end of the L-arm to enable rotation of the C-arm about the location where the C-arm is coupled to the base and to rotate in the orbital direction.

8. The X-ray imaging system of claim 6, wherein the motorized system is configured to rotate the C-arm at least 180 degrees in the orbital direction by rotating the C-arm about the three different rotational axes at pre-defined non-linear rates.

9. The X-ray imaging system of claim 6, wherein the motorized system is configured to rotate the C-arm at least 180 degrees in the orbital direction by rotating the C-arm about the three different rotational axes at different times.

10. An X-ray imaging system, comprising:
an X-ray radiation source;
an X-ray detector;
a C-arm having the X-ray radiation source disposed on a first end and the X-ray detector disposed on a second end opposite the first end;
a base;
a horizontal arm coupled to the base;
an L-arm having a first end and a second end, wherein the first end is coupled to the horizontal arm;
a C-arm rotation device configured to enable the C-arm to rotate in an orbital direction relative to the C-arm rotation device, wherein the C-arm rotation device is coupled to the second end of the L-arm; and
a motorized system configured to rotate the C-arm about three different rotational axes;
wherein a first rotational axis of the three different rotational axes comprises an orbital axis defined by rotation of the C-arm in the orbital direction relative to where the C-arm is coupled to the C-arm rotation device, a second rotational axis of the three different rotational axes comprises a lateral axis defined by rotation of the L-arm about the horizontal arm, and a third rotational axis of the three different rotational axes comprises a flip-flop axis defined by rotation of the C-arm rotation device about the second end of the L-arm.

11. The X-ray imaging system of claim 10, wherein the motorized system is configured to rotate the C-arm at least 180 degrees in the orbital direction about the orbital axis.

12. The X-ray imaging system of claim 11, wherein the motorized system is configured to rotate the C-arm at least 180 degrees in the orbital direction about the orbital axis by both rotating the C-arm 180 degrees about the lateral axis and rotating the C-arm 180 degrees about the flip-flop axis.

13. The X-ray imaging system of claim 10, wherein the base comprises a wheeled base, and the X-ray imaging system comprises a mobile X-ray imaging system.

* * * * *